United States Patent
McGill

(10) Patent No.: US 10,646,417 B2
(45) Date of Patent: May 12, 2020

(54) DENTIFRICE COMPOSITION

(71) Applicant: Glaxo Group Limited, Brentford, Middlesex (GB)

(72) Inventor: Heather McGill, Weybridge (GB)

(73) Assignee: Block Drug Company, Inc., Ewing, NJ (US)

(*) Notice: Subject to any disclaimer, the term of this patent is extended or adjusted under 35 U.S.C. 154(b) by 0 days.

(21) Appl. No.: 14/913,721

(22) PCT Filed: Sep. 2, 2013

(86) PCT No.: PCT/EP2013/068063
§ 371 (c)(1),
(2) Date: Feb. 23, 2016

(87) PCT Pub. No.: WO2015/028096
PCT Pub. Date: Mar. 5, 2015

(65) Prior Publication Data
US 2016/0213581 A1  Jul. 28, 2016

(51) Int. Cl.
| | | |
|---|---|---|
| *A61Q 11/00* | (2006.01) | |
| *A61K 8/19* | (2006.01) | |
| *A61K 8/24* | (2006.01) | |
| *A61K 8/34* | (2006.01) | |
| *A61K 8/39* | (2006.01) | |
| *A61Q 19/00* | (2006.01) | |
| *A61K 8/81* | (2006.01) | |

(52) U.S. Cl.
CPC .......... *A61K 8/19* (2013.01); *A61K 8/24* (2013.01); *A61K 8/345* (2013.01); *A61K 8/39* (2013.01); *A61K 8/8147* (2013.01); *A61Q 11/00* (2013.01); *A61Q 19/00* (2013.01); *A61K 2800/31* (2013.01)

(58) Field of Classification Search
CPC .......... A61K 8/19; A61K 8/24; A61K 8/8147; A61K 8/345; A61K 8/39; A61K 2800/31; A61Q 11/00
See application file for complete search history.

(56) References Cited

U.S. PATENT DOCUMENTS

| | | | |
|---|---|---|---|
| 4,418,057 A | 11/1983 | Groat et al. | |
| 4,726,943 A * | 2/1988 | Klueppel | A61Q 11/00 424/49 |
| 5,882,630 A * | 3/1999 | Gates | A61K 8/25 424/49 |
| 2003/0165442 A1* | 9/2003 | Baig | A23G 4/06 424/57 |
| 2006/0141072 A1 | 6/2006 | Arvanitidou et al. | |
| 2007/0025928 A1 | 2/2007 | Gladorf | |
| 2013/0095045 A1* | 4/2013 | Groves | A61K 8/24 424/52 |

FOREIGN PATENT DOCUMENTS

| | | |
|---|---|---|
| WO | WO 03/045344 | 6/2003 |
| WO | WO 2011/053291 | 5/2011 |
| WO | WO 2011/160996 | * 12/2011 |

* cited by examiner

*Primary Examiner* — Lezah Roberts
(74) *Attorney, Agent, or Firm* — Roshni A. Sitapara; Joshua C. Sanders

(57) ABSTRACT

The present invention relates to a dentifrice composition comprising a stannous salt e.g., stannous fluoride and a water-soluble alkali metal tripolyphosphate e.g., sodium tripolyphosphate and a non-aqueous carrier and wherein the composition is substantially free of any water and does not comprise a source of zinc ions or an aqueous buffer system.

2 Claims, No Drawings

DENTIFRICE COMPOSITION

This application is a 371 national phase entry of International Application No. PCT/EP2013/068063, filed 2 Sep. 2013.

FIELD OF THE INVENTION

The present invention relates generally to an anhydrous dentifrice composition comprising a stannous salt e.g. stannous fluoride and a water-soluble alkali metal tripolyphosphate e.g. sodium tripolyphosphate.

BACKGROUND OF THE INVENTION

Stannous salts are commonly known for their efficacy in oral healthcare. For example stannous fluoride has a long history of use in oral care products for protection against caries, pathogenic bacteria, plaque, gingivitis, dentine hypersensitivity and oral malodor. However there are some disadvantages associated with the use of stannous salts in oral care products, such as chemical instability, astringent taste and tooth discoloration as a result of build-up of extrinsic stannous stain. Accordingly oral care dentifrices containing stannous salts, such as stannous fluoride, have been formulated as dual phase compositions, in which the stannous salt is stabilized in a separate phase from the rest of the composition. The stannous is stabilized without increasing the negative aesthetics associated with stannous and ingredients commonly used to stabilize stannous. However dual-compartmented packages are typically considerably more expensive to manufacture than the conventional laminate tubes that have been used for many years to contain and dispense dentifrice products. Dual-phase products are also less convenient than single phase compositions in terms of ease of use by consumers.

Sodium tripolyphosphate is well-known both as an effective anticalculus (anti-tartar) agent and as an anti-stain agent. However chemical binding of stannous using pyrophosphates, diphosphonates or tripolyphosphates to prevent stain formation also produces unacceptable losses in therapeutic potential, according to U.S. Patent Application Publication No. 2005/0112070 A1). This patent application favours the use of alternative polyphosphates, namely those having an average chain length greater than four, in stannous-containing dentifrice systems.

Other attempts to provide efficacious dentifrice compositions comprising a stannous salt and polyphsophates are described in PCT patent applications WO2007/062365 and WO2011/053291.

WO2007/062365, ("Stannous Salt and Sodium Tripolyphosphate Oral Care Compositions and Methods") describes oral care compositions comprising; (a) about 0.01 to about 5% stannous salt; (b) about 0.01 to about 15% sodium tripolyphosphate; (c) less than about 10% by weight water; and (d) about 0.1 to about 15% by weight of a methylvinyl ether-maleic anhydride copolymer; wherein the composition comprises less than about 1% of stannous tripolyphosphate ionic intermediates.

WO2011/053291, ("Dentifrice Comprising Stannous Fluoride Plus Zinc Citrate and Low Levels of Water") describes dentifrice compositions having a low water phase comprising effective amounts of polyphosphate and ionic active ingredients. More specifically WO2011/053291 describes compositions comprising in a single phase: an orally acceptable vehicle; a source of fluoride ions; a source of stannous ions; a source of zinc ions; and at least one polyphosphate salt selected from the group consisting of inorganic polyphosphate salts which have equal to or less than three phosphorous atoms and wherein the dentifrice composition has a total water content of less than about 10% based on the weight of the composition.

According to WO2011/053291, the compositions therein may further comprise an aqueous buffer system e.g. a citrate buffer system, for the source of stannous ions. Example 1 therein discloses Formulas A, B, C and D comprising inter alia a source of zinc ions (zinc citrate); stannous fluoride and sodium tripolyphosphate (STP). Formulas A and B further comprise a citric acid buffer system whereas Formulas C and D, do not. When Formulas A and C were tested in an accelerated aging study to determine the stability of the stannous salt, Formula A was reported as showing only a small reduction (about 7%) in stannous availability, whereas Formula C showed a large reduction in stannous tin availability (about 33%) and so a formula such as Formula C, would not be stable throughout the normal shelf life of a dentifrice product (typically 12-24 months under ambient temperature).

Whilst dentifrice compositions comprising actives such as stannous salts and polyphosphates have been described in the prior art, it remains challenging to provide these actives in a stable single phase composition. Accordingly it is the aim of the present invention to provide such a composition and in particular which provides good long term storage stability, consistent with the requirements of a commercial dentifrice product.

SUMMARY OF THE INVENTION

Accordingly, the present invention relates to a dentifrice composition comprising a stannous salt, a water-soluble alkali metal tripolyphosphate, a non-aqueous carrier and wherein the composition is substantially free of any water and does not comprise a source of zinc ions or an aqueous buffer system.

These and other features, aspects and advantages of the invention will become evident to those of skill in the art from a reading of the present disclosure.

DETAILED DESCRIPTION OF THE INVENTION

The dentifrice composition of the present invention may be in the form of a toothpaste or dentifrice. The term "dentifrice", as used herein, means paste or gel formulations unless otherwise specified.

As used herein, the word "comprising" encompasses "consisting of" and "consisting essentially of".

As used herein, the word "about", when applied to a value for a parameter of a composition indicates that the calculation or measurement of the value allows some slight imprecision without having a substantial effect on the chemical or physical attributes of the composition.

It has now been found that a dentifrice composition according to the invention comprising a stannous salt, a water-soluble alkali metal tripolyphosphate, a non-aqueous carrier and wherein the composition is substantially free of any water and does not comprise a source of zinc ions or an aqueous buffer system, remains stable throughout the normal shelf life of a dentifrice product. This is surprising given the teaching in the above noted WO2011/053291 publication that low water compositions comprising stannous fluoride and STP demonstrate an unacceptable reduction in stannous availability in the absence of an aqueous buffer system.

Suitably a composition of the present invention is also free of a methylvinyl ether-maleic anhydride copolymer.

A composition of the present invention demonstrates good long-term storage stability, commensurate with that required for a commercial dentifrice. In one embodiment a composition according to the invention demonstrates advantageously a twenty four month product shelf-life. In an accelerated aging study the said composition stored under an ICH (International Conference on Harmonisation of Technical Requirements for Registration of Pharmaceuticals for Human Use) condition of 40° C./75% Relative Humidity (RH) for twelve months exhibited no less than 75% availability of stannous ion and tripolyphosphate at the twelve month time point.

A dentifrice composition of the present invention is substantially free of any water. This is achieved by not adding water to the composition, by not using an aqueous carrier(s) and, where possible, by avoiding the use of components in their hydrated form. Suitably a component selected for use in the composition will be in its anhydrous form. Whilst recognizing that individual components of the composition may contain limited amounts of free and/or bound water, it is essential that the overall composition remains substantially free of any water. Aqueous carriers of the type commonly used in dentifrice compositions are avoided in the present invention; these include for example aqueous solutions of sodium lauryl sulphate, aqueous solutions of sodium hydroxide and aqueous solutions of colouring agents. The total amount of water (both free and bound water) in a composition of the invention is kept to a minimum. Suitably a composition of the invention will comprise less than 0.5% water by weight of the composition, suitably less than 0.2% water by weight of the composition, and even more suitably is 0.0% water by weight of the composition.

A dentifrice composition according to the present invention includes a stannous ion source in the form of a stannous salt. Suitable stannous salts include stannous fluoride, stannous chloride dihydrate, stannous acetate, stannous gluconate, stannous oxalate, stannous sulphate, stannous lactate, stannous tartrate and mixtures thereof. In one embodiment the stannous salt comprises stannous fluoride. The stannous salt may be present in a composition according to the invention in an amount ranging from about 0.05% to about 5%, for example from about 0.1% to about 2% by weight of the composition.

A composition according to the invention is both stable and efficacious and, relative to other known stannous-containing dentifrices, has only a low level of staining and other negative aesthetics, such as astringency.

A dentifrice composition according to the present invention includes a water-soluble alkali metal tripolyphosphate. Suitably the sodium form of this salt may be used, although the potassium or mixed sodium and potassium salts may also be used. Most suitably the water soluble alkali metal tripolyphosphate salt is sodium tripolyphosphate. In one embodiment the anhydrous form of sodium tripolyphosphate is used in a composition of the invention.

Suitably the water soluble alkali metal tripolyphosphate salt is present in an amount ranging from about 1.0% to about 20.0%, for example from about 2.0% to about 10.0% or about 3.0% to about 7.0% by weight of the composition.

A dentifrice composition according to the present invention comprises a non-aqueous carrier. Suitably the carrier comprises a thickening agent, a formulation solvent and a surfactant. Optionally, a dentally acceptable abrasive may be included in the non-aqueous carrier.

Advantageously, a thickening agent is present in the composition to give the product a rheology closer to that of a conventional dentifrice. In one embodiment the thickening agent is a carboxyvinyl polymer such as a carbomer. A carbomer is synthetic high molecular-weight cross-linked polymer of acrylic acid. The polymer chains formed of repeating units of acrylic acid may be cross-linked with, for example: allyl sucrose to provide a carbomer available commercially in one form as Carbopol™ 934; ethers of pentaerythritol to provide a carbomer available commercially in one form as Carbopol™ 974; or with divinyl glycol, available commercially in one form as Noveon™ AA-1. Carbopol™ polymers are manufactured by B.F. Goodrich Company. In one embodiment the carboxyvinyl polymer is Carbopol™ 974. The carboxyvinyl polymer may be present in the range of from about 0.1% to about 7.5% by weight of the dentifrice composition. In one embodiment the carboxyvinyl polymer is present in an amount from about 0.3% to about 1.0% by weight of the composition.

In one embodiment the thickening agent may further comprise an inorganic thickening agent. In one embodiment the thickening agent comprises a combination of a carboxyvinyl polymer and a thickening silica. Suitably, the inorganic thickening agent is a thickening silica available commercially for example as Sident 22S. In one embodiment the thickening silica is present in the range of from about 0.1% to about 15%, suitably from about 5.0% to about 10.0% by weight of the composition.

Suitably the non-aqueous carrier for use in the invention comprises a formulation solvent. Suitably the formulation solvent is selected from glycerin, sorbitol, propylene glycol, polyethylene glycol polymers such as PEG 300 (a polyethylene glycol with an average molecular weight of between 285-315) and PEG 400 (a polyethylene glycol with an average molecular weight of between 380-420), and mixtures thereof. The formulation solvent is used to make the formulation up to 100%, and suitably the total amount of solvent may be present in the range of from about 20% to about 95% by weight of the composition. Suitably the total amount of the formulation solvent is present in an amount from about 65% to about 95% by weight of the composition.

In one embodiment the solvent comprises glycerin. Suitably the composition comprises glycerin present from about 35% to about 75% by weight of the composition. In one embodiment the glycerin is present from about 50% to about 70% by weight of the composition.

It is well known that commercially available glycerin may contain between 0.1-2.0% by weight of water which is in association with the glycerin. Typically this amount is <0.5% for example between 0.1-0.5% by weight of the glycerin. This small amount of water is bound to the glycerin and is therefore not available to the other ingredients. The skilled person would still consider a composition containing glycerin as being non-aqueous. The solvent should in any case be as anhydrous as possible. In one embodiment comprising glycerin the total water content of the composition consists essentially of bound water associated with the glycerin.

In one embodiment the solvent comprises polyethylene glycol. Suitably the polyethylene glycol is selected from PEG300, PEG 400 and mixtures thereof. In one embodiment the polyethylene glycol is PEG 400. Suitably the solvent comprises polyethylene glycol present from about 0.1% to about 40% by weight of the composition. In one embodiment the polyethylene glycol is present from about 15% to about 25% by weight of the composition.

In one embodiment the non-aqueous formulation solvent is a mixture e.g. a mixture of glycerin and a polyethylene glycol. Suitably the glycerin may be present in an amount from about 50% to about 70% by weight of the dentifrice and the polyethylene glycol may be present in an amount from about 15% to about 25% by weight of the dentifrice.

Suitably the carrier for use in the invention comprises a surfactant. A surfactant is usually added to dentifrice products to provide cleaning and/or foaming properties. Any conventional surfactant used in dentifrice formulations may be used in the present invention, provided that it can be added as a solid powder that is not in an aqueous solution. Suitable surfactants include anionic, cationic, nonionic and amphoteric surfactants. Suitable nonionic surfactants include, for example polyoxethoxylated sorbital esters, in particular polyethoxylated sorbitol monoesters. Suitable anionic surfactants include, for example sodium lauryl sulphate, which may be obtained and used in a powder form in the present invention. Suitably the surfactant is present in the range from about 0.1% to about 5% by weight of the dentifrice.

A dentally acceptable abrasive may optionally be added to the dentifrice composition. Advantageously, the presence or absence of a dentally acceptable abrasive as well as the amount of such abrasive may be used to selectively control the abrasivity of the dentifrice composition.

Suitable abrasives for use in the non-aqueous composition include, for example, amorphous, gelled, precipitated or fumed silica, zinc orthophosphate, sodium bicarbonate (baking soda), plastic particles, alumina, hydrated alumina, calcium carbonate, calcium pyrophosphate, insoluble metaphosphates or mixtures thereof.

Generally, an amount of abrasive suitable for use in the dentifrice composition of the present invention will be empirically determined to provide an acceptable level of cleaning and polishing, in accordance with the techniques well known in the art. Suitably, the abrasive may be present in an amount from about 0% to about 60%, typically from about 5% to about 30%, by weight of the dentifrice composition.

The silica abrasive may be a natural amorphous silica, for instance diatomaceous earth; or a synthetic amorphous silica such as a precipitated silica. By way of example, silica abrasives include those marketed under the following trade names Zeodent, Sident, Sorbosil or Tixosil by Huber, Evonik, PQ Corporation and Rhodia respectively.

Suitably when the abrasive comprises a silica, the silica abrasive is present in an amount up to 25% by weight of the total composition, for example from 2% to 20% by weight for example from 5% to 15% by weight of the composition.

The dentifrice compositions of the invention may additionally optionally contain one or more oral care active agents conventionally used in dentifrice compositions, for example a fluoride source, a desensitizing agent, an antierosion agent, an antibacterial agent, an antiplaque agent, an anticalculus agent, an oral malodor agent, an anti-inflammatory agent, an antioxidant, an antifungal agent, would healing agent or a mixture of at least two thereof. Such agents may be included at levels to provide the desired therapeutic effect. Such agents may include, by way of example, a fluoride source and/or an anti-erosion agent or a mixture thereof.

Suitable sources of fluoride ions for use in the compositions of the present invention include an alkali metal fluoride such as sodium fluoride, an alkali metal monofluorophosphate such a sodium monofluorophosphate, stannous fluoride, or an amine fluoride in an amount to provide from 25 to 3500 pm of fluoride ions, preferably from 100 to 1500 ppm. In one embodiment the fluoride source comprises stannous fluoride.

Examples of desensitizing agents include a tubule blocking agent or a nerve desensitizing agent and mixtures thereof, for example as described in WO02/15809 (Block). Examples of desensitizing agents include a strontium salt such as strontium chloride, strontium acetate or strontium nitrate or a potassium salt such as potassium citrate, potassium chloride, potassium bicarbonate, potassium gluconate and especially potassium nitrate.

A desensitizing agent such as a potassium salt is generally present between 2% to 8% by weight of the composition, for example 5% by weight of potassium nitrate may be used.

In one embodiment the desensitizing agent comprises a bioactive glass. Suitably the bioactive glass consists of about 45% by weight silicon dioxide, about 24.5% by weight sodium oxide, about 6% by weight phosphorus oxide, and about 24.5% by weight calcium oxide. One such bioactive glass is available commercially under the trade name, NovaMin®, also known as 45S5 Bioglass®.

Suitably the bioactive glass is present in an amount ranging from about 1 to about 20% by weight of the dentifrice, such as from about 1% to about 15%, or such as from about 1% to about 10%, or such as from about 2% to about 8% by weight of the dentifrice composition.

Compositions of the invention may further comprise an antierosion agent, for example a polymeric mineral surface active agent as described in WO 04/054529 (Procter & Gamble).

Compositions of the present invention will contain additional formulating agents such as flavouring agents, sweetening agents, opacifying or colouring agents and preservatives, selected from those conventionally used in an oral hygiene composition art for such purposes.

In general, the optional agents may be used in a minor amount or proportion of the overall formulation. By way of example, such components are usually present in from about 0.001 to about 5% by weight of the dentifrice composition.

The dentifrice composition typically has a viscosity suitable for application to the oral cavity. The viscosity will vary depending on the type of dentifrice composition made and the ultimate use thereof. One of skill in the art can readily prepare compositions with suitable viscosities for use in the oral cavity from the teachings provided herein.

The compositions according to the present invention may be prepared by admixing the ingredients in the appropriate relative amounts in any order that is convenient.

The invention is further illustrated by the following Examples.

Example 1

Dentifrice Composition

| Ingredient Name | Function | % w/w |
| --- | --- | --- |
| Glycerin | Formulation Solvent | 55.146 |
| PEG-8 | Formulation Solvent | 20.000 |
| Silica | Abrasive and Thickening | 14.400 |
| Sodium tripolyphosphate | Anti-stain, whitening agent | 5.000 |
| Flavour | Flavour | 1.200 |
| Sodium Lauryl Sulphate | Surfactant | 1.100 |
| Titanium Dioxide | Opacifier | 1.000 |
| Carbomer Homopolymer | Thickener | 0.840 |
| Sodium saccharin | Sweetener | 0.500 |
| Stannous Fluoride | Anticavity, antisensitivity agent | 0.454 |
| Cocoamidopropyl Betaine | Surfactant | 0.360 |
| Total | | 100.000 |

Example 2

Formal Stability

Stability data were generated under ICH conditions using the accelerated conditions of 40° C./75% RH, for a composition according to Example 1 above. Table 1 below shows the results obtained for the stannous ion and tripolyphosphate levels over a nine month testing period.

Results

TABLE 1

Stability data at ICH condition 40° C./75% RH

| Timepoint | Method | Stannous Ion (% w/w) | Calculated Percent (%) | Tripolyphosphate (% w/w) | Calculated Percent (%) | pH (1:3 dilution) |
| --- | --- | --- | --- | --- | --- | --- |
| Initial | | 0.302  0.303 | 88.1 | 3.30  3.25 | 95.3 | 7.0 |
| 2 weeks | | 0.302 | 87.8 | 3.01 | 87.5 | 7.1 |
| 1 month | | 0.306 | 89.0 | 3.08 | 89.5 | 7.1 |
| 3 months | | 0.275 | 79.9 | 2.69 | 78.2 | 7.2 |
| 20 months | | 0.285 | 82.8 | 2.87 | 83.4 | 7.0 |
| 6 months | | 0.266 | 77.3 | 3.07 | 89.2 | 7.1 |
| 9 months | | 0.270 | 78.5 | 3.00 | 87.2 | 7.2 |
| 12 months | | 0.263 | 76.5 | 3.01 | 87.5 | 7.2 |

CONCLUSION

Both the stannous ion and tripolyphosphate levels were maintained at a level greater than 75% availability at the twelve month time point following storage under ICH conditions of 40° C./75% RH. This result demonstrates that the composition had been formulated to provide stable conditions for both the stannous ion and the tripolyphosphate components. This finding is further supported by the product pH remaining essentially unchanged at neutral pH for the twelve month period.

The invention claimed is:

1. A single-phase dentifrice composition comprising
    about 0.45% by weight stannous fluoride;
    about 5% by weight sodium tripolyphosphate as an anti-stain agent;
    and a non-aqueous carrier, wherein the said non-aqueous carrier comprises about 55% by weight of glycerin, about 20% weight of polyethylene glycol, about 14% by weight of an abrasive and thickening silica, about 0.8% by weight of a carbomer polymer, about 1.1% by weight of sodium lauryl sulphate, about 0.4% by weight of cocoamidopropyl betaine, and one or more flavouring agents and opacifiers;
    and wherein the composition is free of any water and does not comprise a source of zinc ions or an aqueous buffer system.

2. The dentifrice composition according to claim 1 wherein the composition exhibits no less than 75% availability of stannous ion and tripolyphosphate after storage at 40° C. and a relative humidity of 75% for 12 months.

* * * * *